United States Patent [19]

Draber et al.

[11] 3,941,800
[45] Mar. 2, 1976

[54] N-BENZYLTRIAZOLE COMPOUNDS

[75] Inventors: Wilfried Draber, Wuppertal-Elberfeld; Erik Regel, Wuppertal-Cronenberg; Karl-Heinz Büchel, Wuppertal-Elberfeld; Ludwig Eue, Cologne; Robert R. Schmidt, Leverkusen-Rheindorf, all of Germany

[73] Assignee: Bayer Aktiengesellschaft, Leverkusen, Germany

[22] Filed: Oct. 12, 1973

[21] Appl. No.: 405,969

Related U.S. Application Data

[62] Division of Ser. No. 96,574, Dec. 9, 1970, Pat. No. 3,801,590.

[30] Foreign Application Priority Data

Dec. 24, 1969 Germany............................ 1964995

[52] U.S. Cl............................................. 260/308 R
[51] Int. Cl.².................................... C07D 249/08
[58] Field of Search ............................ 260/308 R

[56] References Cited
UNITED STATES PATENTS

| | | | |
|---|---|---|---|
| 3,682,950 | 8/1972 | Buchel et al..................... | 260/308 R |
| 3,709,901 | 1/1973 | Draber et al..................... | 260/308 R |
| 3,755,345 | 8/1973 | Regel et al...................... | 260/308 R |
| 3,755,349 | 8/1973 | Timmler et al. ................. | 260/308 R |
| 3,870,726 | 3/1975 | Jager et al....................... | 260/308 R |

OTHER PUBLICATIONS
Draber et al., Chem. Abstracts, Vol. 75, Abstract No. 76798k (1971).

*Primary Examiner*—Richard J. Gallagher
*Assistant Examiner*—David E. Wheeler
*Attorney, Agent, or Firm*—Burgess, Dinklage & Sprung

[57] ABSTRACT

Novel N-benzyltriazoles of the formula

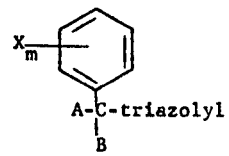

in which
triazolyl is 1,2,4 or 1,2,3 triazolyl which may be substituted;
X is halogen, trifluoromethyl, lower alkyl, lower alkoxy, lower alkylthio, aryl, nitro, cyano or (alkylated) amino;
m is 0, 1 or 2;
A is optionally substituted phenyl, pyridyl, alkyl or cycloalkyl; and
B is a 5-membered heterocyclic ring, e.g., N-heterocycle;
and their salts are outstandingly effective in regulating plant growth, e.g., inhibiting, stimulating or altering plant growth.

5 Claims, No Drawings

N-BENZYLTRIAZOLE COMPOUNDS

This is a division of application Ser. No. 96,574 filed Dec. 9, 1970, now U.S. Pat. No. 3,801,590.

The present invention relates to certain new N-benzyltriazole compounds, to compositions containing them and to their use as agents for the regulation of plant growth.

It is known that succinic acid 2,2-dimethylhydrazide, 2-chloroethyltrimethylammonium chloride and maleic acid hydrazide can be used for regulating the growth of higher plants (see Cathey, H.M., "Physiology of Growth-Retarding Chemicals", Ann. Rev. Plant Phys. 15, pages 271 – 302 (1964), German Published Specification 1,238,052 and U.S. Pat. Nos. 2,575,954; 2,614,912; 2,614,916; 2,614,917 and 2,805,926). The activity of the said compounds of the prior art at low concentrations of active compound is, however, in many cases unsatisfactory and, at high concentrations, in some cases, plant damage occurs.

Surprisingly, the novel N-benzyltriazole compounds of this invention show generally stronger plant-growth-influencing activity than the compounds of the prior art. The compounds according to the invention therefore represent an enrichment of the art.

The compounds of this invention are N-benzyltriazoles of the formula

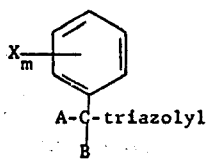

(I)

in which
"triazolyl" is

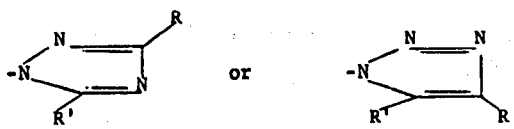

wherein
R and R' are selected independently from the group consisting of hydrogen, lower alkyl and lower alkenyl; and
each X is halogen, trifluoromethyl, lower alkyl, lower alkoxy, lower alkylthio, aryl, nitro, cyano, amino or dialkylamino, e.g., di(lower alkyl)amino;
m is 0, 1 or 2,
A is optionally substituted phenyl or pyridyl, alkyl, e.g., lower alkyl, or cycloalkyl, e.g., cycloalkyl of from 4 to 7 ring carbon atoms; and
B is a five-membered heteroaromatic ring of the general formula

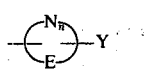

wherein
E is oxygen or sulfur or a radical of the formula

or

and Y is hydrogen, lower alkyl, halogen or an optionally substituted aryl radical, and
n is 0, 1 or 2,
and their salts.

The compounds of the invention exhibit strong plant-growth-regulating properties.

Of the salts of the substituted N-benzyltriazoles of the formula (I), those of acids tolerated by plants are, of course, preferred for the treatment of plants. Examples of such acids are the halogen hydracids, phosphoric acids, sulfonic acids, aliphatic mono- and di-carboxylic acids as well as hydroxycarboxylic acids.

The present invention also provides a process for the production of the compounds according to the present invention, in which a benzyl halide of the formula

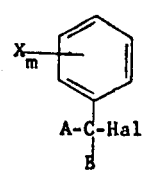

(II)

in which
X, m, A and B have the meanings stated above, and
Hal stands for a chlorine or bromine atom
is reacted with a triazole of the formula

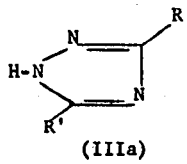 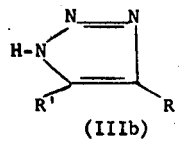

(IIIa)    (IIIb)

in which
R and R' have the meanings stated above in the presence of a diluent, preferably a polar organic solvent, and an acid-binding agent, and, if required, the resulting N-benzyltriazole is converted into a salt thereof.

If phenyl-4-fluorophenyl-(5-methylisoxazol-3-yl)-chloromethane and 1,2,4-triazole are used as starting materials, the reaction course can be represented by the following equation:

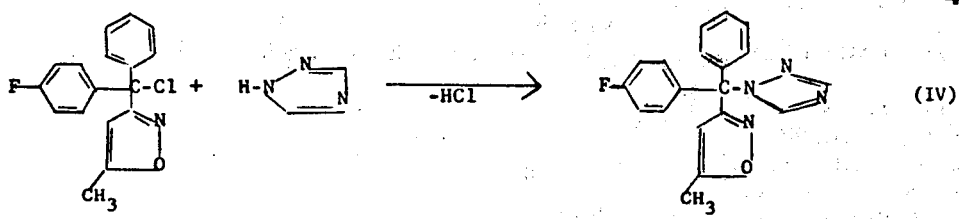

The benzyl halides to be used as starting materials are defined by the above formula (II). In this formula, as in formula (I), X stands preferably for fluorine, chlorine, phenyl, alkyl with up to 3 carbon atoms, methoxy, methylmercapto, trifluoromethyl, nitro, cyano, amino, or dimethylamino, while $m$ stands preferably for 0 or 1. A stands preferably for phenyl or for 2-, 3-, or 4-pyridyl. B stands preferably for one of the following radicals:

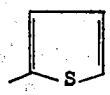 2-thienyl

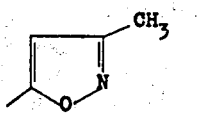 5-(3-methyl)-isoxazolyl

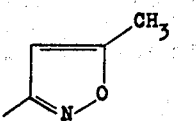 3-(5-methyl)-isoxazolyl

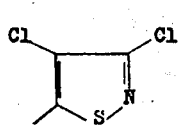 5-(3,4-dichloro)-isothiazolyl

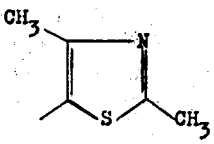 5-(2,4-dimethyl)-thiazolyl

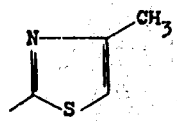 2-(4-methyl)-thiazolyl

 2-(1-methyl)-imidazolyl

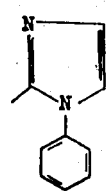 2-(1-phenyl)-imidazolyl

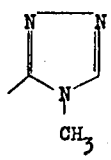 3-(4-methyl)-1,2,4-triazolyl

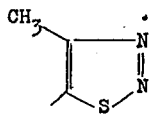 5-(4-methyl)-1,2,3-thiadiazolyl

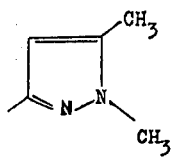 5-(2,3-dimethyl)-pyrazolyl

As examples of the benzyl halides which can be used in the preparative process according to the invention, there may be mentioned:
bis-phenyl-(thien-2-yl)-chloromethane
bis-phenyl-(3-methyl-isoxazol-5-yl)-chloromethane
phenyl-4-fluorophenyl-(5-methyl-isoxazol-3-yl)-chloromethane
phenyl-4-chlorophenyl-(1-methyl-imidazol-2-yl)-chloromethane
phenyl-diphenylyl-(1-methyl-imidazol-2-yl)-chloromethane
phenyl-4-methylmercaptophenyl-(3-methyl-isoxazol-5-yl)-chloromethane
phenyl-4-methylmercaptophenyl-(5-methyl-isoxazol-3-yl)-chloromethane
phenyl-4-chlorophenyl-(5-methyl-isoxazol-3-yl)-chloromethane
phenyl-4-fluorophenyl-(3-methyl-isoxazol-5-yl)-chloromethane
phenyl-4-tert.-butylphenyl-(1-methyl-imidazol-2-yl)-chloromethane
phenyl-3-methylphenyl-(1-methyl-imidazol-2-yl)-chloromethane
phenyl-3-trifluoromethyl-(1-methyl-imidazol-2-yl)-chloromethane
phenyl-4-nitrophenyl-(thien-2-yl)-chloromethane
(pyrid-4-yl)-phenyl-(3-methyl-isoxazol-5-yl)-chloromethane
phenyl-4-methoxyphenyl-(5-methyl-isoxazol-3-yl)-chloromethane The benzyl halides of the formula (II) are new but can be prepared by reacting a carbinol of the general formula

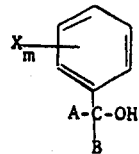 (V)

in which
A, B, X and m have the meanings stated above with an agent for halogenating tertiary alcohols. Especially suitable halogenating agents are acid chlorides, such as thionyl chloride, thionyl bromide, phosphoryl bromide, phosphoryl chloride, phosphorus trichloride, phosphorus tribromide, acetyl chloride and acetyl bromide. The reaction can be carried out either in the absence or presence of a solvent; suitable solvents include ethers, methylene chloride, benzene and toluene. The reaction is carried out at temperatures of 0° to 150°C., preferably at 20° to 120°C. If the five-membered heterocyclic substituent of the carbinol (V) contains nitrogen, the halides (II) are frequently obtained in the form of their halogen hydracid salts.

The triazoles to be used as starting materials are defined by the formulae (IIIa) and (IIIb). In these formulae, R and R' stand preferably for hydrogen, methyl or ethyl. The 1,2,4-triazolyl derivatives (IIIa) are preferred. As an example, there may be mentioned 1,2,4-triazole, which is known.

As diluents for the reaction of the halide (II) with the triazole (IIIa) or (IIIb), especially suitable are polar organic solvents, the preferred solvents being nitriles (such as acetonitrile), nitromethane, dimethyl formamide, hexamethyl-phosphoric acid triamide, acetone and chloroform.

As the acid-binding agent, an excess of the triazole (IIIa) or (IIIb) is suitable. Organic bases of low nucleophilicity, such as triethylamine, lutidine, quinoline, or inorganic bases, such as potassium carbonate, magnesium oxide or calcium carbonate, can also be used.

The reaction temperatures can be varied within a fairly wide range. In general, the work is carried out at from 0° to 150°C. preferably from 20° to 100°C.

When carrying out the process according to the invention, the triazole is expediently used in at least the equivalent amount. If one wishes to dispense with an auxiliary agent for acid-binding purposes, the triazole should be used in at least twice the molar (equivalent) amount, and in three times the molar (equivalent) amount if a hydrohalide of the formula (II) is used. If an auxiliary agent is employed for acid-binding, this should be used in at least the equivalent amount, preferably in excess.

A preferred embodiment of the process comprises adding dropwise a solution of the halide (II) to a solution of the triazole (IIIa) or (IIIb), which also contains the acid-binding agent for example triethylamine, in a polar organic solvent, such as acetonitrile, at an elevated temperature, preferably at 70° to 80°C.

It may furthermore be expedient to carry out, in one of the above-mentioned polar solvents, the preliminary halogenation of the appropriate carbinol (V) and to follow directly, without intermediate isolation of the resulting halide, with the reaction according to the invention using a suitable triazole.

Working up is effected in any customary manner, for example by concentration, washing with water, and recrystallization The compounds can also be made to separate by addition of water.

The active compounds according to the invention interfere with the physiological phenomena of plant growth and can therefore be used as plant-growth regulators.

The different effects of an active compound depend essentially on the point in time of the application, with reference to the development stage of the seed or the plant, as well as on the concentration applied.

Plant-growth regulators are used for various purposes which are connected with the development stage of the plant.

Thus, with plant-growth regulators the seed dormancy can be broken in order to cause the seeds to germinate at a certain desired time at which the seed itself shows no readiness to germinate. The seed germination itself can either be inhibited or promoted by such active compounds, depending on the concentration applied. This inhibition or promotion relates to the seedling development.

The bud dormancy of the plants, that is to say the endogenic annual cycle, can be influenced by the active compounds, so that the plants, for example, shoot or blossom at a point in time at which they normally show no readiness to shoot or blossom.

The shoot or root growth can be promoted or inhibited by the active compounds in manner dependent on the concentration. Thus, it is possible to inhibit very strongly the growth of the fully formed plant, or to bring the plant as a whole to a more robust habitus or to produce a drawf growth.

A use of the active compounds which is of economic interest is the suppression of grass growth at roadsides and waysides. Further, the growth of lawns can be inhibited by growth regulators, so that the frequency of grass-cutting (of lawn-mowing) can be reduced.

During the growth of the plant, the branching to the side can be multiplied by a chemical breaking of the apical dominance. This can be utilized in, for example, the case of propagation of plants by cuttings. In a manner dependent on the concentration of the compounds it is also possible to inhibit the growth of side-shoots, for example in order to prevent, in tabacco plants, the formation of side-shoots after decapitation and thus to promote the leaf growth.

In the case of the influencing of blossom formation, there can be achieved, in a manner dependent on the concentration and the point in time of the application, either a retarding or an acceleration of blossom formation. Under certain circumstances, a multiplication of blossom initiation can also be obtained, these effects occurring when the appropriate treatments are carried out at the time of the normal blossom formation.

The influence of the active compounds on the foliage of the plants can be so regulated that a defoliation is achieved, for example in order to facilitate harvesting or to reduce transpiration at a time at which the plants are to be transplanted.

Fruit initiation can be promoted so that more, or seedless, fruits are formed (parthenocarpy). Under certain conditions, the premature fall of fruit can also be prevented, or the fruit fall can be promoted to a certain extent in the sense of a chemical thinning out. The promotion of the fruit fall can, however, also be so exploited that the treatment is effected at the time of the harvest, thereby facilitating the harvesting.

The active compounds according to the present invention can be converted into the usual formulations, such as solutions, emulsions, suspensions, powders, pastes and granulates. These may be produced in known manner, for example by mixing the active compounds with extenders, that is, liquid or solid diluents or carriers, optionally with the use of surface-active agents, that is, emulsifying agents and/or dispersong agents. In the case of the use of water as an extender, organic solvents can, for example, also be used as auxiliary solvents.

As liquid diluents or carriers, there are preferably used aromatic hydrocarbons, such as xylenes or benzene, chlorinated aromatic hydrocarbons, such as chlorobenzenes, paraffins, such as mineral oil fractions, alcohols, such as methanol or butanol, or strongly polar solvents, such as dimethyl formamide or dimethyl sulfoxide, as well as water.

As solid diluents or carriers, there are preferably used ground natural minerals, such as kaolins, clays, talc or chalk, or ground synthetic minerals, such as highly-dispersed silicic acid or silicates.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulfonates and aryl sulfonates; and preferred examples of dispersing agents include lignin, sulfite waste liquors and methyl cellulose.

The formulations contain, in general, between 0.1 and 95, preferably between 0.5 and 90, per cent by weight of active compound.

The active compounds may be applied as such or in the form of their formulations or of the application forms prepared therefrom, such as ready-to-use solutions, emulsifiable concentrates, emulsions, suspensions, spray powders, pastes, soluble powders, dusting agents and granulates. Application takes place in any customary manner, for example by watering, squirting, spraying, scattering cr dusting.

The concentrations of active compound for actual application can be varied within a fairly wide range. In general, concentrations of 0.005 to 2%, preferably from 0.01 to 0.5%, are used.

Furthermore, there are applied, in general, 0.1 to 100 kg, preferably 1 to 10 kg, of active compound per hectare of soil area.

For the application time, it is usually valid to say that application is most favorable when a strong elongation growth has occurred, that is at the so-called "time of greatest shooting". In ligneous plants, application is preferred shortly before commencement of shooting. Thus, in contrast to the application of insecticides and fungicides, the application of the growth regulators is preferably effected in a given space of time, the precise delimitation of which is governed by the climatic and vegetative circumstances.

The present invention also provides a plant-growth-regulating composition containing as active ingredient a compound of the present invention in admixture with a solid diluent or carrier or in admixture with a liquid diluent or carrier containing a surface-active agent.

The present invention also provides a method of controlling the growth of plants which comprises applying to the plants or seeds thereof a compound of the present invention alone or in the form of a composition containing as active ingredient a compound of the present invention in admixture with a solid or liquid diluent or carrier.

Some of the compounds to be used according to the invention are also effective against plant-damaging fungi (for example against mildew species) and bacteria. An activity against mold fungi and yeasts has also been noted.

The activity of the compounds according to the invention can be seen from the following Examples, in which the following test compounds illustrative of the invention were employed:

TABLE

| Compound No. | Chemical Name | Structure |
|---|---|---|
| 1 | (4-fluoro-phenyl)-phenyl-(5-methyl-isoxazol-3-yl)-(1,2,4-triazol-1-yl)-methane | 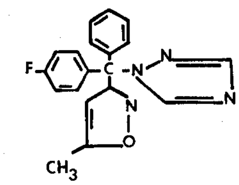 |
| 2 | (4-chloro-phenyl)-phenyl-(5-methyl-isoxazol-3-yl)-(1,2,4-triazol-1-yl)-methane | 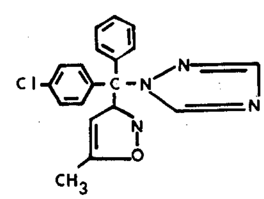 |
| 3 | (3-methyl-phenyl)-phenyl-(1-methyl-imidazol-2-yl)-(1,2,4-triazol-1-yl)-methane | 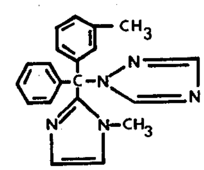 |
| 4 | bis-phenyl-(5-methyl-isoxazol-3-yl)-(1,2,4-triazol-1-yl)-methane | 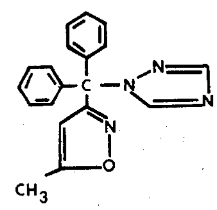 |
| 5 | (4-fluoro-phenyl)-phenyl-(5-methyl-isoxazol-3-yl)-(1,2,4-triazol-1-yl)-methane | 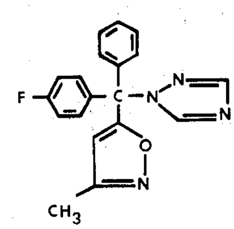 |

TABLE-continued

| Compound No. | Chemical Name | Structure |
|---|---|---|
| 6 | (4-chloro-phenyl)-phenyl-(1-methyl-imidazol-2-yl)-(1,2,4-triazol-1-yl)-methane | (structure) |
| 7 | (4-tert.-butyl-phenyl)-phenyl(1-methyl-imidazol-2-yl)-(1,2,4-triazol-1-yl)-methane | (structure) |
| 8 | (4-phenyl-phenyl)-phenyl(1-methyl-imidazol-2-yl)-(1,2,4-triazol-1-yl)-methane | (structure) |

EXAMPLE A

Growth inhibition/linseed test

Solvent: 40 parts by weight acetone
Emulsifier: 0.25 parts by weight alkylaryl polyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Batches of 25 linseeds were laid out on two filter papers in a Petri dish. 10 ml. of the preparation of active compound were pipetted into each dish. Germination of the seeds took place in the dark at 25°C.

After 3 days, the length of the roots was determined and the growth inhibition compared with the control plant was expressed as a percentage. 100% denoted the standstill of growth, and 0% denoted a growth corresponding to that of the untreated plant.

The active compounds, the concentrations of the active compounds in ppm (=mg/kg) and results can be seen from the following Table.

TABLE A

| Active compound | % inhibition with | |
|---|---|---|
| | 50 ppm | 250 ppm |
| water (control) | 0 | 0 |
| succinic acid 2,2-dimethylhydrazide (known) | 12 | 15 |
| (2-chloroethyl)-trimethyl-ammonium chloride (known) | 20 | 30 |
| maleic acid hydrazide (known) | 36 | 50 |
| Compound 1 | 85 | 100 |
| Compound 2 | 55 | 85 |
| Compound 3 | 85 | 100 |

EXAMPLE B

Growth inhibition/oat grains

Solvent: 40 parts by weight acetone
Emulsifier: 0.25 parts by weight alkylaryl polyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Batches of 25 oat grains were laid out on two filter papers in a Petri dish. 10 ml. of the preparation of active compound were pipetted into each dish. Germination of the seeds took place in the dark at 25°C.

After 3 days, the length of the shoot was determined and the growth inhibition compared with the control plant was expressed as a percentage. 100% denoted the standstill of growth, and 0% denoted a growth corresponding to that of the untreated plant.

The active compounds, concentrations of the active compounds in ppm (=mg/kg) and the results can be seen from the following Table.

TABLE B

| Active Compound | Growth inhibition / oat grains test | |
|---|---|---|
| | % inhibition with | |
| | 50 ppm | 250 ppm |
| water (control) | 0 | 0 |
| succinic acid 2,2-dimethyl hydrazide (known) | 22 | 37 |
| (2-chloroethyl)-trimethyl-ammonium chloride (known) | 22 | 31 |
| maleic acid hydrazide (known) | 20 | 40 |
| Compound 1 | 97 | 100 |
| Compound 2 | 55 | 95 |
| Compound 4 | 65 | 75 |
| Compound 5 | 80 | 90 |
| Compound 6 | 25 | 70 |
| Compound 7 | 25 | 62 |

EXAMPLE C

Growth inhibition/apple seedlings

Solvent: 40 parts by weight acetone
Emulsifier: 0.25 parts by weight alkylaryl polyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Apple seedlings were, at a height of about 2 cm, sprayed with a preparation which contained 500 ppm of active compound.

After 7 days, the percentage inhibition of the treated plants compared with the untreated control plant was determined. With 100% inhibition, no growth was present; with 0% inhibition, the growth corresponded to that of the control plant.

The active compounds, the concentrations of the active compounds in ppm (=mg/kg) and the results can be seen from the following Table.

TABLE C

| Active compound | Growth inhibition / apple seedlings test |
|---|---|
| | % inhibition with 500 ppm |
| water (control) | 0 |
| succinic acid 2,2-dimethylhydrazide (known) | 23 |
| (2-chloroethyl)-trimethyl-ammonium chloride (known) | 25 |
| Compound 1 | 50 |
| Compound 4 | 43 |
| Compound 5 | 57 |

EXAMPLE D

Growth inhibition/tomato plants

Solvent: 40 parts by weight acetone
Emulsifier: 0.25 parts by weight alkylaryl polyglycol ether To produce a suitable preparation of active compounds, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Tomato plants of a height of 10 cm were sprayed with a preparation which contained 500 ppm of active compound.

After 8 days, the percentage inhibition of the treated plants compared with the untreated control plant was determined. With 100% inhibition, no growth was present; with 0% inhibition, the growth corresponded to that of the control plant.

The active compounds, concentration of active compound in ppm (=mg/kg) and the results can be seen from the following Table.

TABLE D

| Active compound | Growth inhibition / tomato plants test |
|---|---|
| | % inhibition with 500 ppm |
| water (control) | 0 |
| succinic acid-2,2-dimethylhydrazide (known) | 20 |
| (2-chloroethyl)-trimethyl-ammonium chloride (known) | 25 |
| maleic acid hydrazide (known) | 33 |
| Compound 1 | 81 |
| Compound 2 | 88 |
| Compound 4 | 80 |

TABLE D-continued

Growth inhibition / tomato plants test

| Active compound | % inhibition with 500 ppm |
|---|---|
| Compound 5 | 71 |
| Compound 3 | 60 |

Example E

Growth inhibition/bean plants

Solvent: 40 parts by weight acetone
Emulsifier: 0.25 parts by weight alkylaryl polyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentrations.

Beans (Phaseolus vulgaris) 10 cm high were sprayed with preparations which contained 500 ppm of active compound.

After 8 days, the length of the treated plants compared with the untreated control plant was determined.

The active compounds, concentrations of active compound in ppm (=mg/kg) and the results can be seen from the following Table.

TABLE E

Growth inhibition / beans

| Active compounds | Length in cm with a concentration of active compound of 500 ppm |
|---|---|
| water (control) | 26 |
| maleic acid hydrazide (known) | 12 |
| Compound 1 | 10.5 |
| Compound 2 | 10.0 |
| Compound 5 | 10.0 |
| Compound 8 | 11.5 |

The following Example illustrates the preparative process of the present invention.

EXAMPLE 1

Preparation of bis-phenyl-(3-methylisoxazol-5-yl)-(1,2,4-triazol-1-yl)-methane

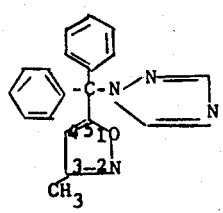

Preliminary product:

21 grams (0.08 mole) bis-phenyl-(3-methylisoxazol-5-yl)-carbinol were boiled in 250 ml methylene chloride with 10.1 grams (0.085 mole) thionyl chloride until the evolution of gas ceased. The solution was concentrated in a vacuum. Reaction:

The bis-phenyl-(3-methylisoxazol-5-yl)-chloromethane obtained above was without isolation, dissolved in 150 ml. acetonitrile, and the solution was added dropwise to a boiling solution of 16.6 grams (0.24 mole) 1,2,4-triazole in 100 ml. acetonitrile. The mixture was boiled for 30 minutes, concentrated, and ice water was added to the residue. 20.2 grams bis-phenyl-(3-methylisoxazol-5-yl)-1,2,4-triazol-1-yl)-methane of the melting point 167°–169°C. were obtained in the form of colorless crystals.

Yield: 79% of the theory (with reference to the carbinol used as preliminary product).

Starting material

The carbinol required as a starting material was obtained in the following manner:

From 31.4 grams (0.2 mole) bromobenzene and 4.86 grams (0.2 mole) magnesium turnings in 150 ml ether there was prepared a solution of phenylmagnesium bromide which was added dropwise at −5°C to a solution of 18.7 grams (0.1 mole) 5-benzoyl-3-methylisoxazole. Heating was effected slowly, followed by boiling under reflux for one hour and poured onto ice. After acidification with 25 ml hydrochloric acid, the ethereal phase was separated; washing with bicarbonate solution was effected, followed by drying and concentration. The residue was crystallized with ether/petroleum ether. 21 grams bis-phenyl-(3-methylisoxazol-5-yl)-carbinol of the melting point 116°–118°C. were obtained.

Yield: 80% of the theory.

The following compounds were prepared in an analogous manner:

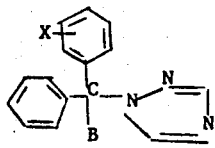

| Example No. | X | B | m.p.(°C) |
|---|---|---|---|
| 2 | 4-F | 5-methyl-isoxazol-3-yl | 99–100 |
| 3 | 4-Cl | 1-methyl-imidazol-2-yl | 142 |
| 4 | 4-⟨C₆H₅⟩ | 1-methyl-imidazol-2-yl | 135 |
| 5 | 4-SCH₃ | 3-methyl-isoxazol-5-yl | 94–97 |
| 6 | 4-SCH₃ | 5-methyl-isoxazol-3-yl | 116–117 |
| 7 | 4-Cl | 5-methyl-isoxazol-3-yl | 104–106 |
| 8 | 4-F | 3-methyl-isoxazol-5-yl | 127–128 |
| 9 | 4-C(CH₃)₃ | 1-methyl-imidazol-2-yl | 130 |
| 10 | 3-CH₃ | 1-methyl-imidazol-2-yl | 120 |

It will be understood that the foregoing specification and examples are illustrative and not limitative of the present invention in that many other embodiments of the invention will suggest themselves to those skilled in the art.

What is claimed is:

1. N-benzyltriazole compound of the formula

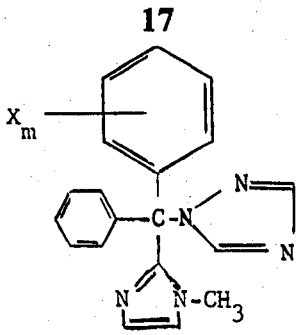

wherein
X is chlorine, alkyl with 1 to 4 carbon atoms or phenyl, m is 0 or 1;
and salts thereof with plant-tolerated acids.

2. Compound as claimed in claim 1 designated as (3-methyl-phenyl)-phenyl-(1-methyl-imidazol-2-yl)-(1,2,4-triazol-1-yl)-methane.

3. Compound as claimed in claim 1 designated as (4-chloro-phenyl)-phenyl-(1-methyl-imidazol-2-yl)-(1,2,4-triazol-1-yl)-methane.

4. Compound as claimed in claim 1 designated as (4-tert.-butyl-phenyl)-phenyl-(1-methyl-imidazol-2-yl)-(1,2,4-triazol-1-yl)-methane.

5. Compound as claimed in claim 1 designated as (4-phenyl-phenyl)-phenyl-(1-methyl-imidazol-2-yl)-(1,2,4-triazol-1-yl)-methane.

* * * * *